United States Patent [19]
Chang

[11] Patent Number: 5,713,889
[45] Date of Patent: Feb. 3, 1998

[54] URETHRAL STUMP CARRIER FOR RADICAL RETROPUBIC PROSTATECTOMY

[76] Inventor: Hau Hsien Chang, 7704 Calle Espada, Bakersfield, Calif. 93309

[21] Appl. No.: 261,821

[22] Filed: Jun. 20, 1994

Related U.S. Application Data

[63] Continuation-in-part of Ser. No. 963,762, Oct. 20, 1992, abandoned.

[51] Int. Cl.⁶ .................................................. A61B 19/00
[52] U.S. Cl. .................................................................. 606/1
[58] Field of Search ........................... 604/19, 35, 164, 604/264, 275, 902; 606/1, 108

[56] References Cited

U.S. PATENT DOCUMENTS

| | | | |
|---|---|---|---|
| 3,963,028 | 6/1976 | Cooley et al. | 604/902 |
| 4,904,238 | 2/1990 | Williams | 604/35 |
| 5,141,501 | 8/1992 | Adkinson et al. | 604/19 |

*Primary Examiner*—Glenn Dawson

[57] ABSTRACT

A smooth blunt tip tubular structure in a form of a sound or a catheter and a pressure producing and regulating system. The sound or the catheter has a smooth blunt end on one end and a non blunted end on the opposite end. There is a lumen extending from one end to the opposite end. There is a furrow running circumferentially around the blunt end of the sound or the catheter. The furrow lies on the side wall within two centimer from the blunt end tip of the sound or the catheter. There are multiple openings on the floor of the furrow. The openings within the furrow communicate with the lumen of the sound or the catheter. The pressure producing end regulating system is in fluid communication with the lumen. The side walls of the furrow elevate above the surface of the sound or the catheter forming ridges. There are six grooves equally distanced from each other between the furrow and the tip of the sound or the catheter. With the entire system in operative condition, the tip of the sound or the catheter is able to carry by suction, the transected segment of membranous urethra to the pelvis for it to be anastomosed to the bladder neck at the time of radical retropubic prostatectomy.

6 Claims, 3 Drawing Sheets 5,713,889

URETHRAL STUMP CARRIER FOR RADICAL RETROPUBIC PROSTATECTOMY

This application is a CIP of U.S. Ser. No. 07/963,762, filed on Oct. 20, 1992, now abandoned.

BACKGROUND OF THE INVENTION

1. Field of the Invention

The invention relates an improved device with a different working mechanism and principle from the conventional instrument to carrying the retracted distal segment of membranous urethra, thereafter called the urethral stump, from the urogenital diaphragram of the pelvis into the pelvis for easy anastomosis of said urethral end to the bladder neck in a procedure called Radical Retropubic Prostatectomy.

2. Description of the Prior Art.

In an operation called "Radical Retropubic Prostatectomy" for the treatment of a patient with a localized cancer of the prostate, the membranous urethra is identified distal to the apex or distal tip of the prostate. The membranous urethra is transected and the prostate is removed. The distal segment of the transected membranous urethra, thereafter called the Membranous Urethral Stump, is sutured to the bladder neck with absorbable sutures. It happens that in most instances, the urethral stump retracts and recedes within the muscle of the pelvic floor, the urogenital diaphragram, and cannot be seen again. Anastomosis of the urethral stump to the bladder neck, therefore became extremely difficult and sometimes impossible. Prior inventions consist of using urethral sounds or catheters of larger diameter than the urethra to push or carry the urethral stump into the pelvis for anastomosis. The principle of the prior art rely on the friction formed between the sound and the urethra; since the urethra is an elastic tube, it expands as the instrument is inserted within its lumen. The urethral stump tends to slide back the end of the instrument, it then retracts back into the muscle of urogenital diaphragram. The anastomosis between urethra and the bladder neck becomes impossible.

SUMMARY OF THE INVENTION

The invention is an improved urethral sound or a catheter connected to a fine scale positive and negative pressure generating system. The sound or the catheter can be rigid or flexible, it has an external diameter the same as the diameter of the normal male urethra usually between twenty to twentyfour French in size, there is a smooth central lumen extending from the blunt tip of the sound or the catheter to the opposite non blunt end of the stem of the sound or the catheter. The non blunt end of the stem of the sound or the catheter is connected to a fine scale pressure generating system which is able to produce a positive and a negative pressure and is able to maintain it in a desirable pressure range automatically. The blunt end of the sound is slightly curved if it is a rigid instrument. It can be straight or slightly curved if it is a flexible catheter. The blunt end of the sound or the catheter is smooth and atraumatic. There is a narrow furrow measuring one centimeter in width and less than five milimeters in depth engraved circumferentially on the outer surface of the blunt end segment of the sound or the catheter within one inch from the tip of the blunt end of the sound or the catheter. The valley of the furrow is deepen into the wall of the catheter or the sound. There are multiple openings, whether the openings are small or large, regardless of the numbers of the openings, located at the valley of the furrow. The openings at the valley of the furrow communicate with the lumen of the sound or the catheter. The edges where the side walls of the furrow became in contact with the surface of the sound are elevated. There are two elevated lines or ridges on the surface of the sound or the catheter, one ridge line on each side of the furrow of the sound or the catheter, within one inch proximal to the tip of the sound or the catheter. The ridges lines run circumferentially around the sound or the catheter atop either side walls of the furrow of the sound or the catheter. The tip of the sound or the catheter is blunt ended. There is a single opening less than three mm in size at exactly the tip of the blunt end of the sound or the catheter; the opening at the tip of the blunt end of the sound or the catheter communicates with the central lumen of the catheter. There are six shallow grooves on the lateral surface of the blunt end segment of the catheter or the sound. The grooves locate between the furrow and the tip of the blunt end of the sound or the catheter. The grooves are engraved into the wall of the sound. They are evenly distanced from each other and parallel to the axis of the catheter. After the prostate was removed during the procedure of radical retropubic prostatectomy, the blunt end of the sound or the catheter is inserted into the urethra through the male urethral meatus. The tip of the sound or the catheter is just barely visible in the membranous urethral stump through the pelvis. A desirable negative pressure is created and maintained in the pressure producing system. The negative pressure is transmitted to the lumen of the sound or the catheter. The membranous urethral wall is then aspirated into the furrow of the sound or the catheter. The elevated ridges besides the furrow resist the urethral tissue from sliding back toward the stem of the sound or the catheter as the tip of the sound or the catheter is advanced toward the pelvic cavity. The small hole at the very end of the blunt end of the sound or the catheter works as a sump to prevent the tissue from damaging or developing a hematoma in the area of the urethra near the furrow as the result of the negative pressure aspiration. The urethral stump which was carried from the urogenital diaphragram to the pelvis is therefore ready for anastomosis. After the anastomosis of the the membranous urethra to the bladder neck is completed, the aspirated urethral wall in the furrow of the sound or the catheter is then ejected by a positive pressure generated in the pressure generating system. The urethral sound or the catheter can therefore be removed.

The present invention utilizes a different principle of the physics by creating a negative pressure in the lumen of the sound or the catheter to receive and carry the membranous urethral stump to the pelvis during the surgery.

DESCRIPTION OF THE PREFERRED EMBODIMENT

Figure 1:
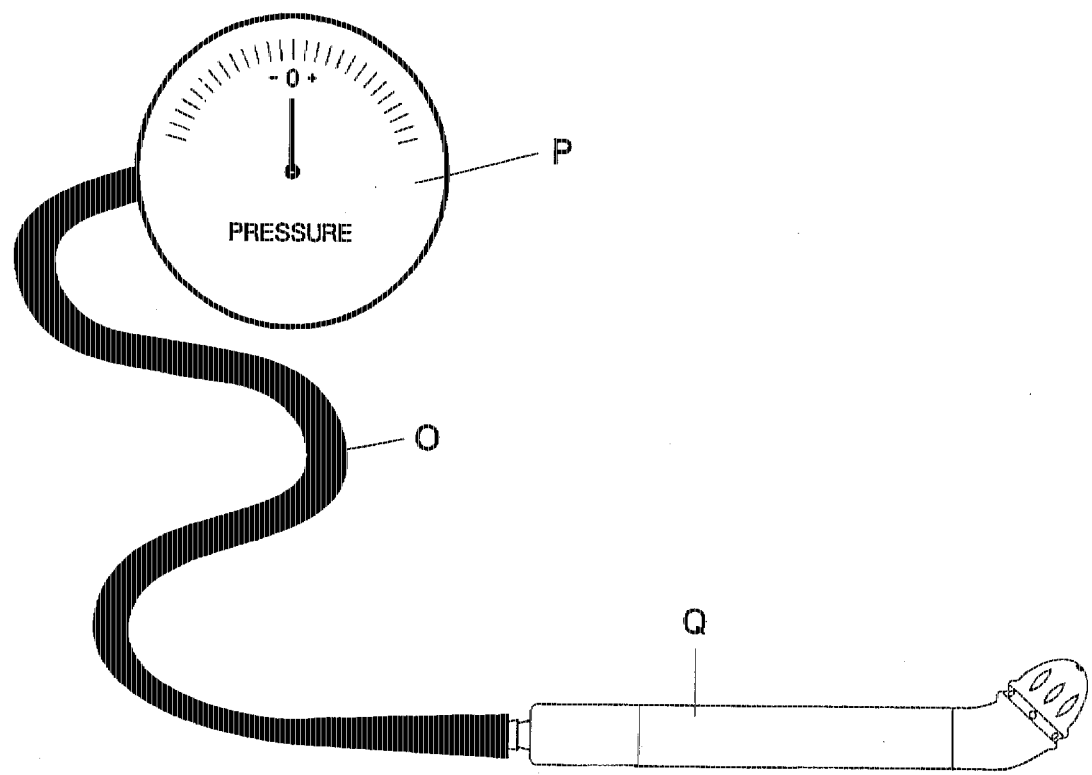
FIG. 1 is external view of urethral stump carrier and the integrated pressure generating and regulating system in connection.

FIG. 1 is external view of the entire system showing the urethral stump carrier "Q" and the pressure generating and regulating system "P" connected together and in operative condition. The urethral stump carrier in the form of the sound or the catheter "Q" is connected to the pressure producing and regulating system "P" with a non collapsable flexible tube "O".

Figure 2:
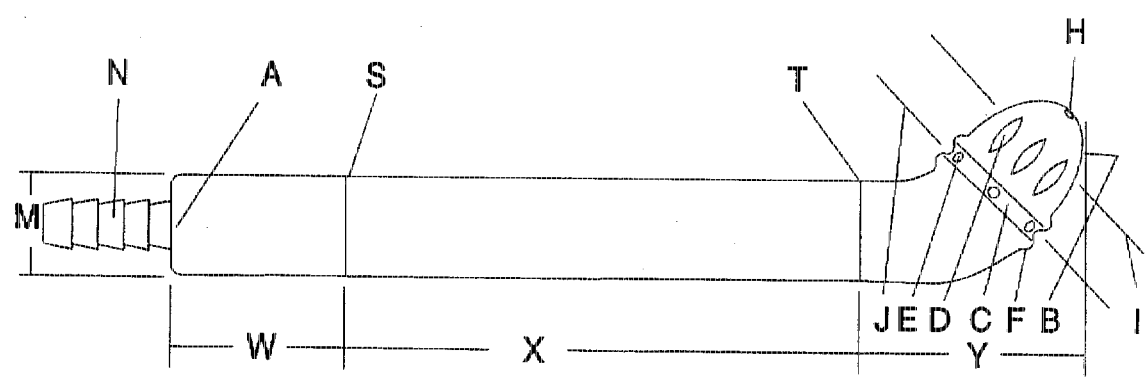
FIG. 2 is a three dimension external view of a urethral stump carrier.
Figure 3:
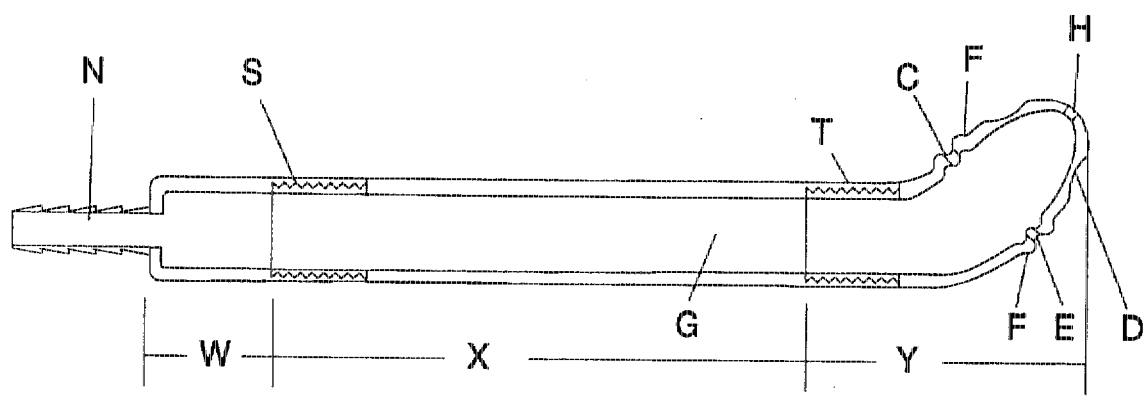
FIG. 3 is a longitudinal section view of the urethral stump carrier.
Figures 4, 5:
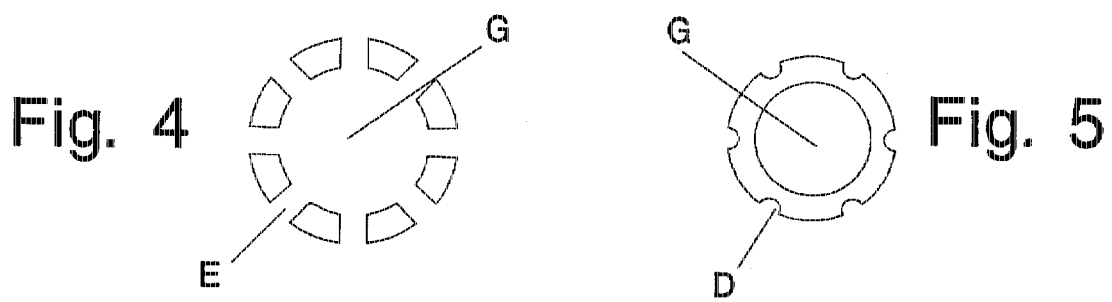
FIG. 4 is a cross section view of the urethral stump carrier at the valley of the furrow, on cross section plane J.
FIG. 5 is a cross section view of the urethral stump carrier at the tip of the sound or the catheter distal to the furrow on cross section plane I.
Figure 6:
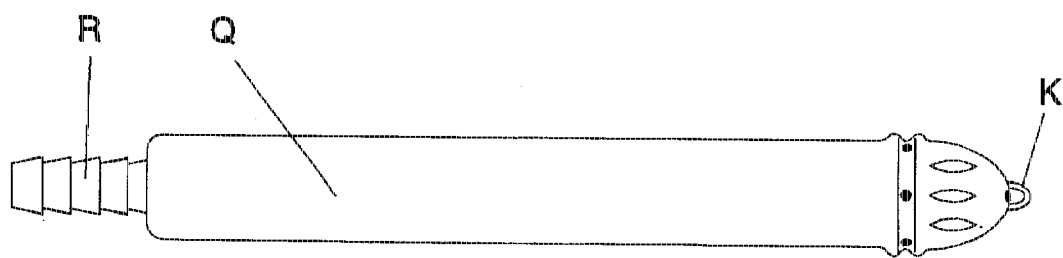
FIG. 6 is a external view of urethral stump carrier in a catheter form with a loop at the tip of the catheter.

FIG. 2 is a external side view of the urethral stump carrier "Q". The distal end of the carrier in the form of the sound or the catheter "B" is smooth and blunted. It tapers slightly toward the tip. The proximal end of the sound or the catheter "A" is open ended, it slightly tapers to a segment of corrugated connecting part "N" where the flexible pressure resistant non collapsable tube "O" from the pressure generating and regulating system (FIG. 1) is connected. The external diameter "M" of the urethral stump carrier should be comparable to the usual male urethral diameter, it usually ranges from twenty to twentyfour French or 6.7 to 8 millimeter in diameter, whereas the length of the sound or the catheter (X plus Y plus W) should be longer than the usual adult male urethral length. The distal end of the sound or the catheter B can be straight or slightly curved. Within two centimeters from the tip of the catheter "B", a deep furrow or a groove "C" lies circumferentially in the wall of the sound or the catheter. There are multiple openings "E's" located at the valley of the furrow. The openings "E's" on the valley of the furrow "C" are equally distanced; the openings penetrate through the entire thickness of the wall of the sound or the catheter. The openings communicate with the central lumen of the catheter "G" (as shown in FIG. 3 and FIG. 4). As the side walls of the furrow rise to intersect with the surface of the sound or the catheter, they form two elevated ridges, "F's" (as shown on FIGS. 1 through 6), proximal and distal to the furrow. Said elevated ridges run circumferentially around the sound or the catheter and parallel to the furrow of the sound or the catheter. There are six ellipse shape grooves "D's", engraved in the side wall of the sound or the catheter distal to the furrow "C", the grooves "D's" are equally distanced from each other and are not in communication with the central lumen of the sound or the catheter "G" (as shown in FIG. 3 and FIG. 5). The grooves designate the sites of the needle placement during the process of anastomosis. At the most distal end of the sound or the catheter a small opening "H" measuring less than three mm in diameter is created, the opening "H" communicates with the lumen of the sound or the catheter "G" (as shown in FIG. 3). In the case of a flexible catheter, a loop attachment "K" is constructed external to the opening at the tip of the catheter for the placement of a suture for the purpose of traction of the catheter during the operation (as shown in FIG. 6). When the urethral sound or catheter carrier "Q" is connected to a pressure generating and regulating system "P" with a pressure resistant tube "O" (as shown in FIG. 1), the system is in an operative condition. The pressure producing system in this invention is able to produce positive and negative pressure and to maintain it at the desirable pressure range. For manufacture and cleaning simplicity, the urethral stump sound or catheter can be divided into three parts, W, X and Y. They are connected together in one piece at S and T where male and female screw threads are located as is shown in FIG. 3. The sound or the catheter can also be made in one piece.

FIG. 3 illustrates the longitudinal section view of the urethral stump carrier "Q". Each letter on the drawing corresponds to the letter shown in other Figures in each embodiment.

FIG. 4 is a cross section view of the urethral stump carrier at the valley of the furrow, on cross section plane "J" (as shown in FIG. 2). The figure illustrates the multiple openings "E's" communicate with the central lumen "G" of the sound or the catheter. The openings "E's" are equally distanced.

FIG. 5 is a cross section view of the urethral stump carrier at the tip of the sound or the catheter "B" distal to the furrow "C" on plaine I (as shown in FIG. 2). The grooves D's are engraved in the wall of the sound or the catheter. The grooves do not communicate with the lumen of the sound or the catheter "G".

FIG. 6 illustrates one of the embodiments of present invention. A straight flexible catheter is made in one piece. The catheter has a loop "K" at the end of the tip the catheter. The loop is made for placement of a suture for the traction of the catheter.

Figure 7:
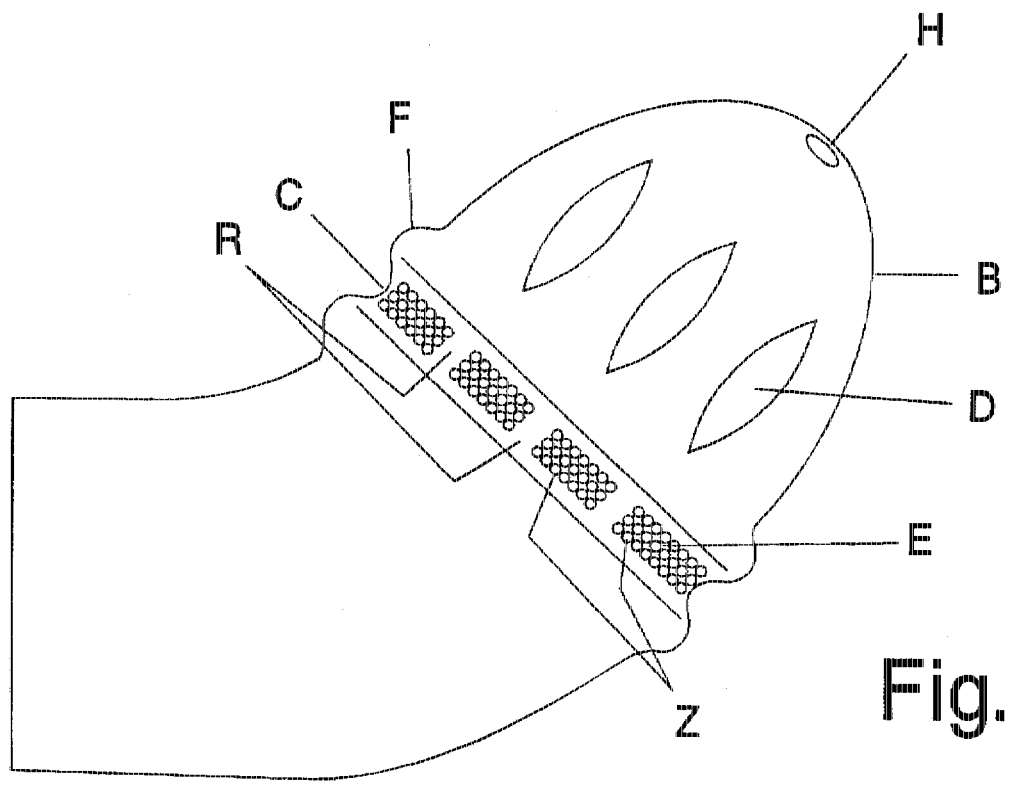
FIG. 7 is a external view of urethral stump carrier showing the mesh like minute holes on the floor of the furrow.

FIG. 7 is a magnification of the external view of the head of the sound showing another embodiment of the present invention with the floor of the furrow full of multiple mesh like opening "Z's". There are multiple bridges "R's" between the meshes. The purpose of forming bridges "R's" between the meshes "Z's" is to maintain a solid attachment of the head of the sound B to the shaft of the sound.

Figure 8:
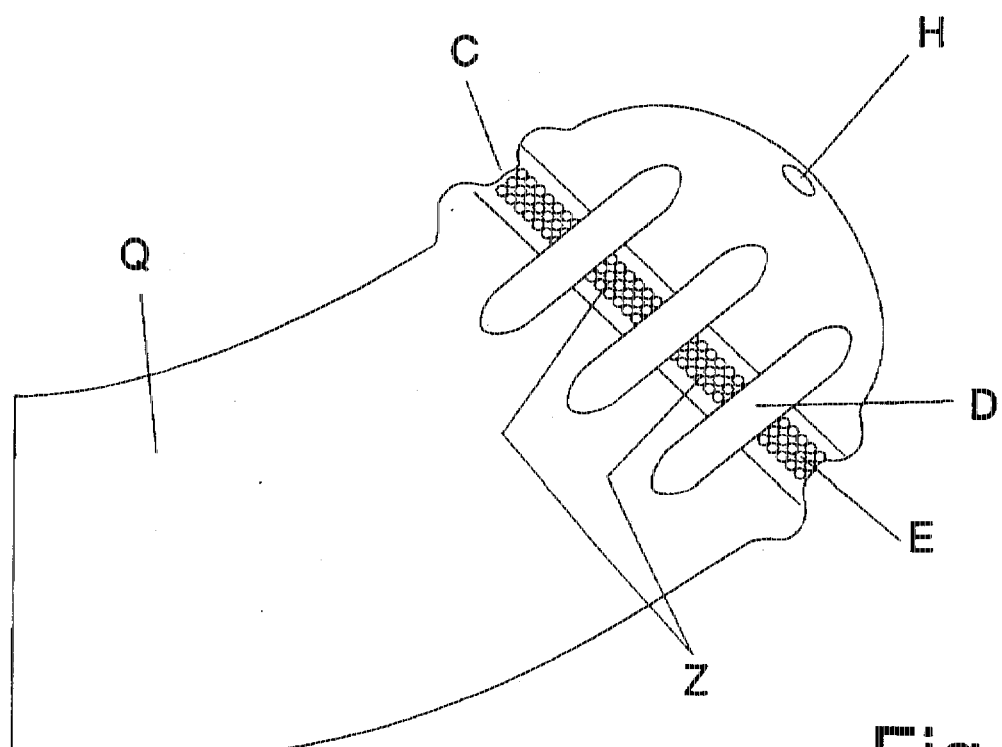
FIG. 8 is a external view of the urethral stump carrier showing the furrow is more distally placed and overlap with the suture grooves.

FIG. 8 is another embodiment of the sound showing the furrow of the sound is more distally located and overlapped with the suture grooves. In the drawing, there are mesh-like openings interposing with the suture grooves. The suture grooves are also the bridges "R's" in this drawing. Although detailed embodiments of the invention and their variants are illustrated in the drawings and previously described in detail, this invention contemplates any configuration, dimention, design and relationships of the components except otherwise specified which will function in a similar manner and which will provide the equivalent result.

I claim:

1. An urethral stump carrier system for bringing a distal segment of a transected membranous urethra from a urogenital diaphragm to a pelvis for easier anastomosis of an urethra to a bladder neck, said system comprising:

a) a long tubular structure in the form of a catheter or a sound; said tubular structure having an open proximal end and a tapered blunt distal end; said tubular structure having a diameter configured to be approximately the same as the diameter of a normal male urethra and a length longer than a normal male urethra; said distal end having an opening, said tubular structure comprising a lumen therethrough connecting both end openings; the opening at the proximal end being larger than the opening at the distal end, said opening at the distal end being less than 3 mm in diameter; said tubular structure comprising a 1 cm. wide and 0.5 cm or less deep furrow running circumferentially in an outer side wall of said tubular structure within 2 cm of a tip of the distal end of the tubular structure; said furrow comprising multiple small openings in a valley of the furrow, said small openings comprising canals communicating with the lumen of the tubular structure; said distal end comprising six grooves engraved in a lateral surface of the side wall of the tubular structure between the furrow and the tip of the distal end, said grooves comprising ellipse shaped indentations in the side wall of the tubular structure parallel to a longitudinal axis of the tubular structure; and b) means to generate and regulate positive and negative pressure in the lumen of the tubular structure and to maintain the pressure at a constant desirable level, said means connected to the open proximal end by a pressure resistant tube therebetween.

2. The urethral stump carrier system according to claim 1, wherein the furrow and the grooves may overlap each other within 2 cm from the tip of the tubular structure.

3. The urethral stump carrier system according to claim 1, wherein side walls of the furrow project radially outwardly from the side wall of the tubular structure forming ridges.

4. The urethral stump carrier system according to claim 1, wherein a segment of the tubular structure within 3 cm from the tip of the tubular structure is slightly curved.

5. The urethral stump carrier system according to claim 1, wherein a segment of the tubular structure within 3 cm from the tip of the tubular structure is straight.

6. The urethral stump carrier system according to claim 1, wherein the tubular structure is constructed from one of the group of materials consisting of metal, plastic, silastic, polyurethane, latex or an equivalent biocompatible material.

* * * * *